United States Patent [19]

Haggiage et al.

[11] Patent Number: 4,746,509

[45] Date of Patent: May 24, 1988

[54] TRANSDERMAL MEDICAMENT

[75] Inventors: Johnny Haggiage, Lyons; Christian Pusineri, Serezin du Rhone, both of France

[73] Assignee: Rhone-Poulenc Sante, Courbevoie, France

[21] Appl. No.: 14,190

[22] Filed: Feb. 3, 1987

Related U.S. Application Data

[63] Continuation of Ser. No. 592,817, Mar. 23, 1984, abandoned.

[30] Foreign Application Priority Data

Mar. 24, 1983 [FR] France ................... 83 04839

[51] Int. Cl.⁴ ............. A61L 15/03; A61F 13/00; A61K 9/70
[52] U.S. Cl. ............................. 424/449; 514/947
[58] Field of Search ............... 424/449; 604/896, 897; 514/947

[56] References Cited

U.S. PATENT DOCUMENTS

| | | | |
|---|---|---|---|
| 3,262,450 | 7/1966 | Elias | 424/28 |
| 3,624,224 | 11/1971 | Wei et al. | 424/28 |
| 3,934,016 | 1/1976 | Roux et al. | 514/871 |
| 3,985,892 | 10/1976 | Roux et al. | 514/871 |
| 4,555,524 | 11/1985 | Gruber et al. | 514/947 |
| 4,695,464 | 9/1987 | Alderman | 424/449 |
| 4,699,779 | 10/1987 | Palinczar | 514/937 |

FOREIGN PATENT DOCUMENTS

| | | |
|---|---|---|
| 2421610 | 4/1979 | France . |
| 2093344 | 9/1982 | United Kingdom . |
| 2095108 | 9/1982 | United Kingdom . |

OTHER PUBLICATIONS

Rieg-Falson, C.A. 105: 66340d (1986).
Jan, C.A. 105: 49085g (1986).
Haggiage, C.A. 102: 137796h (1985).
Roux, C.A. 85: 198178k (1976).
Saito et al, Arzneim. Forsch 33(11)m. 9: 1301-1305 (1983).
Nitto Electric, C.A. 96: 187302x (1982).
CA, 96: 187302x.

*Primary Examiner*—Shep K. Rose
*Attorney, Agent, or Firm*—Stevens, Davis, Miller & Mosher

[57] ABSTRACT

New transdermal medicaments comprise the active ingredient dispersed in a heat-reversible, non-crosslinked, film-forming, homogeneous polymer optionally with a non-ionic emulsifier and, if appropriate, a hydrophobic, water-insoluble copolymer.

18 Claims, No Drawings

TRANSDERMAL MEDICAMENT

This application is a continuation of application Ser. No. 592,817, filed Mar. 23, 1984 now abandoned.

The present invention relates to transdermal medicaments.

More particularly, the invention relates to a new galenical form of medicaments which may be, for example, an antianginal product (isosorbide dinitrate, isosorbide 5-mononitrate and trinitrin), antiemetic product (metopimazine and dimenhydrinate), anticholinergic product (scopolamine), non-steroid anti-inflammatory product (ketoprofen), steroid anti-inflammatory product (prednisolone and dexamethasone), antihypertensive product (clonidine), beta-blocking product (acebutolol), vasodilator product (nicergoline), neuroleptic product (phenothiazines), tranquilliser product (benzodiazepines, suriclone and suproclone), bronchodilator product (phenylpropanolamine), antispasmodic product (butylhyoscine bromide), or hormone (estradiol).

These medicaments, which are active at relatively low doses, require progressive release in the organism to be of maximum effectiveness. In general, these medicaments are used in the form of pressed tablets, tablets which can be administered perorally or sublingually or suppositories. When used in this form, the medicaments have a relatively short duration of action which, for some of them, can be less than 1 hour. Continuous treatment requires the product to be taken at well-defined intervals of time, but without a regular action being obtained. It is particularly important to have available galenical forms which ensure continuous and controlled release of the active principle in the organism to provide as constant an effect as possible over a defined period, which can reach several hours or even several days.

For this purpose, compositions which act by percutaneous absorption and in which the dose administered can be easily controlled and which release the active principle in the organism in a regular manner have been proposed. Such galenical forms facilitate the administration of the active principle. They permit direct access to the systemic circulation without passage through the gastrointestinal tract, and they avoid the first-path effect.

Various systems have been proposed for providing transdermal compositions. For example, according to U.S. Pat. No. 3,797,494, regulation of the release is ensured by a microporous membrane. The system consists of a reservoir component containing the active ingredient, a microporous membrane, and an adhesive for attaching the system on the skin.

A system which does not contain a microporous membrane, the skin of the patient acting as the flow-regulating membrane, can also be used, as described, for example, in European patent application No. 13,606. The active principle is contained in a system based on polyvinyl alcohol and a water-soluble gel based on polyvinylpyrrolidone.

Other preparations have been described, in which latices of silicones or of elastomeric polymers are used, for example, in French Pat. No. 2,497,457 or U.S. Pat. No. 4,336,243.

These various systems may present technological difficulties of implementation or give results which are a function of the sensitivity of the patient, the skin acting as a regulatory membrane.

It has now been found, and this is the object of the present invention, that microporous membranes can advantageously be replaced by homogeneous membranes in which the variable hydrophilicity enables the kinetics of the release of the active ingredient to be controlled.

The new transdermal form of the present invention differs from known systems by the nature of the constituents and by the possibility of regulation of the kinetics of the release of the active ingredient by a process which does not use a microporous membrane.

In the new transdermal medicament, the active ingredient is dispersed in crystalline form and/or, preferably, in a solubilised form in a homogeneous elastomeric matrix with, if necessary, a non-ionic emulsifying agent. By varying the hydrophilic character of the mixture, it is possible to determine and to control the rate of release of the active ingredient.

It is furthermore possible to add to the mixture random or graft copolymers of which one of the sequences or one of the grafts is incompatible with the matrix and has a low surface energy (less than or equal to 30 erg $cm^2$). These sequences or grafts lead to a concentration of copolymer at the surface, forming a homogeneous membrane which permits complementary control of the release, favouring the achievement of zero order kinetics of release. These compounds may be, for example, random or graft copolymers based on polydimethylsiloxane.

To provide the transdermal medicament of the invention, it is particularly advantageous to use heat-reversible, non-crosslinked, film-forming polymers which are insoluble in water but may be water-miscible and in which it is possible to vary the hydrophilic character. The films obtained from these polymers swell in the presence of water (in the form of liquid or vapour) and the degree of swelling can be adjusted by the hydrophilic lipophilic balance of the matrix, the additive and the active ingredient.

More particularly, polyurethane/polyoxyethylene glycol (POEG)/poloxypropylene glycol (POPG) copolymers are suitable for this purpose. It may be advantageous to use polyurethanes based on a polyether or polyester, such as polytetramethylene glycols, polycaprolactones or polyadipates, for example the products marketed under the names Pellethane, Estane or Quinn. Other heat-reversible elastomers can also be used, such as polyamides, polyesters, polyethers or polyolefines.

In general, the hydrophilic (or hydrophobic) character of a copolymer may be determined by the degree of swelling in a humid atmosphere in the following manner: A sample, which has first been weighed, is placed in a saturated humid atmosphere for at least one night at a temperature of about 20° C. The weight of the swollen sample enables the degree of hydration to be calculated, this being directly related to the hydrophilicity of the polymer. For example, in the case of polyurethane/-POEG POPG copolymers, the hydrophilic character is a function of the POEG/POPG ratio. In this case, the copolymer is hydrophilic if the POEG/POPG ratio is greater than 1:1, and it is hydrophobic if the POEG/-POPG ratio is less than 1, the hydrophilic or hydrophobic character being more or less pronounced, depending on the exact value of the ratio.

Dispersion of the active principle in the polymer matrix is ensured by means of non-ionic emulsifiers which are compatible with the polymer matrix and with the active principle, these emulsifiers generally being those used in cosmetology and in pharmacy as ingredients for creams, milks or ointments or as gelling or dispersing agents, or as excipients for suppositories. These non-ionic emulsifiers based on glycol polymers or glycerol polymers are in general polycondensates of ethylene oxide with fatty acids or fatty alcohols, sorbitan esters, triglycerides with free hydroxyl groups, polypropylene glycol monoglycerides or polyglycerol esters. Non-ionic emulsifiers of this type which can be used include, in particular, products manufactured and marketed, for example, by Société Gattefosse, such as Plurol stéarique (polyglycerol palmitostearate), Plurol isostéarique (polyglycerol isostearate), Sucroester WE 15 (sucrose monopalmitate), Labrafil CS 2735 (polyoxyethylene oleyl glyceride), Transcutol (diethylene glycol monoethyl ether) or Labrasol (polyoxyethylene $C_8$-$C_{10}$-glycerides). These non-ionic emulsifiers can also be used as vehicles for transdermal administration.

These non-ionic emulsifiers essentially differ in their hydrophilic/lipophilic balance (HLB) and by their melting point.

The kinetics of release of the active principle can be determined by measuring the amount of released compound which accumulates in a volume of liquid, from a film attached to a support immersed in the liquid, as a function of time in accordance with the method of S. Borodkin and E. F. Tucker, J. Pharm. Sci., 64 (8) 1289-94 (1975). The active ingredient diffuses through the matrix at a rate which depends essentially on the nature of the polymer and the additive used, but which is also a function of other mechanisms, such as the dissolution of the product, if this is crystalline, or the swelling of the matrix.

According to Fick's law, the amount of released product which accumulates as a function of time can be expressed in the following manner:

$$Q = \sqrt{D(2A - Cs)Cp \cdot t} = kr \cdot \sqrt{t}$$

In this formula,

Q represents the amount of separated out-product which accumulates per unit surface area (mg/cm$^2$);
A represents the amount of product in the polymer matrix per unit volume (mg/cc);
Cs and Cp represent the solubility of the product in the liquid and the matrix; and,
D represents the diffusion coefficient of the product in the matrix.

This function can be represented by a straight line, the gradient of which (kr) is proportional to the initial rate of release of the active ingredient.

By studying the influence of various parameters on the value of kr, the composition of the transdermal medicament suitable for the desired effect can be determined.

For example, the influence of the various parameters can be studied in the following manner, using isosorbide dinitrate as the active ingredient, a polyurethane POEG/POPG copolymer as the copolymer, and various emulsifiers.

1. Influence of the hydrophilicity of the copolymer

Films consisting of polyurethane/POEG/POPG copolymers in which the POEG/POPG ratios are 75:25, 50:50 and 25:75 and containing 10% by weight of a non-ionic emulsifier (Plurol stéarique) and 10% by weight of isosorbide dinitrate are prepared and the amount of released active product which accumulates is measured as a function of time.

The results are summarised in Table I.

TABLE I

| Polyurethane/POEG/POPG $R = \dfrac{POEG}{POPG}$ | kr mg/cm$^2 \cdot$ h$^{-\frac{1}{2}}$ | Delay time $t_1$ (hours) |
| --- | --- | --- |
| 75/25 | 1.06 | 0 |
| 50/50 | 0.6 | 0.3 |
| 25/75 | 0.5 | 0.77 |

These results show that the rate of release is higher for a hydrophilic polymer (POEG/POPG=75/25) than for a hydrophobic polymer (POEG/POPG=25/75).

Furthermore, other measurements show that the most hydrophilic polymer adsorbs up to 68% of its weight of water, whilst the most hydrophobic polymer absorbs only about 20%. In all cases, the absorption of water is accompanied by the crystallisation of isosorbide dinitrate in the polymer matrix.

2. Influence of the nature of the non-ionic emulsifier

Films consisting of polyurethane/POEG/POPG copolymer in which the POEG/POPG ratio is equal to 75/25, non-ionic emulsifiers and 10 to 20% of isosorbide dinitrate are prepared. The amount of released active ingredient which accumulates is measured as a function of time.

The results are summarised in Table II.

TABLE II

| Non-ionic emulsifier | % by weight of emulsifier | Isosorbide dinitrate (%) | Film thickness (mm) | kr | Reaction time (hours) |
| --- | --- | --- | --- | --- | --- |
| Sucro-ester WE 15 (solid) | 10 | 20 | 0.12 | 0.27 | 0 |
| | 20 | 10 | 0.21 | 0.83 | 0.13 |
| | 10 | 10 | 0.17 | 0.63 | 0 |
| Plurol stearique (wax) | 10 | 10 | 0.11 | 0.92 | 0 |
| | 10 | 10 | 0.12 | 1.06–1.23 | 0 |
| Labrafil CS 2735 (oily liquid) | 10 | 10 | | 0.95–1.1 | 0.18 |
| | 20 | 10 | 0.1 | 0.72 | 0.13 |
| Plurol iso-stearique (liquid) | 20 | 20 | 0.16 | | 0 |
| | 20 | 10 | 0.17 | | 0 |

From these results, it can be seen that the rate of elution of isosorbide dinitrate is influenced by the lipophilic character and the physical state (solid or liquid) of the emulsifier used.

Thus, Sucro-ester WE 15, although very hydrophilic (hydrophilic/lipophilic balance=15), slows down the rate of elution of isosorbide dinitrate. The rate of elution with Labrafil CS 2735 (hydrophilic/lipophilic balance=3-4) is lower than that with Plurol stéarique (hydrophilic/lipophilic balance=9-10), with a reaction time of 0.13 to 0.18 hour. The high reaction time is associated with the difficulty of swelling of the polymer. The addition of Plurol isostéarique as emulsifying agent leads to an increase in the hydrophilicity of the polymer, which is reflected by a swelling of the polymer.

3. Influence of the concentration of isosorbide dinitrate

Three films based on polyurethane/POEG/POPG copolymer and containing 10% of Plurol stéarique, as the emulsifier, and 10, 20 and, respectively, 30% of isosorbide dinitrate are prepared. The amount of released active ingredient which accumulates is measured as a function of time. The results are summarised in Table III.

TABLE III

| Film | Isosorbide dinitrate % | Film thickness (mm) | kr mg/cm$^2 \cdot$ h$^{-\frac{1}{2}}$ |
|---|---|---|---|
| No. 1 | 10 | 0.23 | 0.85 |
| No. 2 | 20 | 0.20 | 1.15–1.3 |
| No. 3 | 30 | 0.20 | 1.1 |

From these results, it can be seen that the isosorbide dinitrate is released at virtually the same initial rate, independently of the initial amount of active product.

A copolymer film containing 30% of isosorbide dinitrate presents difficulties on storage. In fact, too high a concentration of isosorbide dinitrate causes crystallisation of the active ingredient in contact with the moisture in the air.

To improve the kinetics of the release of the active ingredient, it is particularly advantageous to add to the polyurethane/POEG/POPG matrix a hydrophobic compound which migrates to the surface to form a homogeneous membrane. It is particularly useful to use a polydimethylsiloxane/polyoxyethylene glycol copolymer in which the polydimethylsiloxane sequence is hydrophobic and migrates to the surface to form a homogeneous membrane, whilst the polyoxyethylene glycol sequence imparts compatibility with the matrix.

To demonstrate the usefulness of the addition of a compatible hydrophobic copolymer, it is possible to produce films containing emulsifiers of the same hydrophilicity, one liquid (Plurol isostéarique) and the other solid (Plurol stéarique), and increasing amounts of additives, such as 0, 10 and 30%. The influence of the additive is determined by measuring the amount of active principle released as a function of time. In particular, by using Plurol stéarique as the emulsifier and polydimethylsiloxane/polyoxyethylene glycol in an amount of about 30%, the amount of released active product which accumulates as a function of time is represented by a straight line in the case where the active principle is isosorbide dinitrate.

According to the present invention, the new transdermal medicaments can be obtained by adding a mixture of the active principle and the non-ionic emulsifier in a defined proportion to a mixture of the elastomeric copolymer and an organic solvent, such as dimethylformamide, methyl ethyl ketone, dioxane or methyl isobutyl ketone. The mixture is then poured, by a known technique, onto a suitable support, such as a glass plate or a support of controlled adhesion, such as silicone-coated paper, after some of the solvent has been removed by evaporation under reduced pressure. The film obtained is then dried under reduced pressure in order to eliminate all the solvent, in particular in the case where a solvent of high boiling point is used.

The mixture of the copolymer and an organic solvent is prepared by stirring the elastomeric copolymer and, where relevant, the hydrophobic copolymer in an organic solvent, such as dimethylformamide, at a temperature greater than 50° C. such that a homogeneous mixture is obtained, which is in general in the form of a collodion. In general, the mixture obtained contains 5 to 30% by weight of copolymer or of the mixture of copolymers.

The mixture of the active ingredient and the non-ionic emulsifier is prepared from a solution of the active ingredient in a suitable organic solvent, such as ethyl alcohol or ethyl ether, to which the non-ionic emulsifier is added. The mixture of the active ingredient and the non-ionic emulsifier in the desired proportion is obtained after evaporation of the solvent, if necessary under reduced pressure.

For example, with isosorbide dinitrate, it may be advantageous to prepare films based on polyurethane containing 5 to 20% of isosorbide dinitrate, 5 to 30% of non-ionic emulsifier and, if appropriate, 1 to 30% of hydrophobic additive, the percentages being by weight, based on the polymer used.

For use of the transdermal medicaments according to the invention, it is necessary for the films thus prepared to be in as perfect contact as possible with the skin. For this purpose, an adhesive which may have the properties of a homogeneous membrane, such as a silicone adhesive, may be applied to the surface of the film by crosslinking in the presence of a suitable catalyst.

Other adhesives may be used, such as, for example, those which are described in U.S. Pat. No. 3,797,494. If appropriate, the adhesive may contain the active ingredient. The adhesives may be applied by deposition or by transfer.

Moreover, the films containing the active ingredient may be covered on the surfaces which are not in contact with the skin with materials which are impermeable to release of the active ingredient and which may, in addition, serve to keep the device on the skin.

By way of example, the effectiveness of the transdermal forms according to the present invention in which the active principle isosorbide dinitrate may be demonstrated on animals, and more particularly on pigs.

6 pigs of uniform weight are divided into 3 groups of 2 animals. In each group, one animal receives a defined dose and the other receives twice this dose.

Group A receives a reference cream of 10% of isosorbide dinitrate.

Group B receives a film based on the polyurethane POEG/POPG (75/25) copolymer and the emulsifier Plurol stéarique (10%), and Group C receives a film based on the polyurethane/POEG/POPG (75/25) copolymer and the emulsifier Labrafil CS 2735 (10%).

One animal of a group receives 100 mg of isosorbide dinitrate and the other receives 200 mg of isosorbide dinitrate.

For each group of animals, 5 to 10 cc of blood are withdrawn before the administration of the dose and at regular intervals up to 8 hours after administration. The blood collected over lithium heparinate is kept at +4° C. before being centrifuged at 4,500 revolutions/minute for 10 minutes. The plasma is then preserved at −20° C. until the isosorbide dinitrate is analysed by a method which utilises gas chromatography on a capillary column, with detection by electron capture in accordance with a technique derived from that of H. LAUFEN et al., J. Chromatog., 146, 457 (1978).

The transdermal films are evaluated with respect to the reference cream by:
the development of the plasma concentrations of isosorbide dinitrate in the course of time and the areas under the curves (AUC), which give the concentrations of isosorbide dinitrate as a function of time.

The results are summarised in Table IV.

TABLE IV

Plasma concentrations of isosorbide dinitrate (ISDN) (ng/ml) obtained with the aid of the 3 modes of transcutaneous administration studied. Amounts of ISDN absorbed (expressed by the area under the curvesAUC) starting from the 3 modes of transcutaneous administration studied.

| Reference treatments | Treatment A cream | | Treatment B (emulsifier Plurol) | | Treatment C (emulsifier Labrafil) | |
|---|---|---|---|---|---|---|
| Dose of ISDN absorbed | 100 mg | 200 mg | 13.4 | 47.9 | 28 | 83 |
| "Rate" of ISDN ($\mu$g/minute) | 208.3 | 416.7 | 27.9 | 99.8 | 58.3 | 172.9 |
| Pig No. | 2 | 3 | 4 | 5 | 6 | 7 |
| (sex; weight) | F - 27.7 kg | F - 28.4 kg | F - 27.7 kg | M - 28.5 kg | M - 24.4 kg | M - 25.3 kg |
| Time of withdrawal | Plasma concentrations of isosorbide dinitrate (ng/ml) | | | | | |
| 0 | 0 | 0 | 0 | 0 | 0 | 0 |
| 1 hour | 3.60 | 42.65 | 0 | 0.65 | 0 | 0 |
| 2 hours | 7.10 | 7.40 | 1.20 | 0.40 | 1.0 | 1.85 |
| 4 hours | 5.60 | 8.95 | 17.30 | 5.55 | 2.85 | 1.30 |
| 6 hours | 6.95 | 10.25 | 2.25 | 2.05 | 2.75 | 1.25 |
| 8 hours | 3.15 | 10.45 | 1.60 | 2.10 | 1.75 | 1.90 |
| $AUC_{0\to 8}$ hours (hours · ng · ml$^{-1}$) | 42.50 | 102.60 | 42.50 | 18.55 | 14.45 | 9.78 |
| $AUC_{0\to 8}$ hours standardised for the dose (hours · ng · ml$^{-1}$ · mg$^{-1}$) | 0.425 | 0.513 | 3.172 | 0.387 | 0.516 | 0.118 |
| $AUC_{0\to 8}$ hours standardised dose and weight | 11.77 | 14.57 | 87.86 | 11.03 | 12.59 | 2.98 |

*calculated according to the equation $= \dfrac{AUC_{0\to 8} \text{ hours}}{\text{dose/weight}} = \dfrac{AUC_{0\to 8} \text{ hours} \times \text{weight}}{\text{dose}}$ The results show, in particular, that the films and the cream tested differ, in the first place, by the amount of isosorbide dinitrate absorbed. In fact, although absorption is 100% complete within 8 hours for the cream, it is only 15 to 25% complete for the films.

Absorption is greater from films containing Labrafil. This difference in the doses absorbed is also found in the plasma concentrations of isosorbide dinitrate. Furthermore, for all the films tested, these concentrations reach levels which have always proved to be effective in human therapy.

The investigation of the amounts absorbed into the plasma indicates that absorption from films is more effective the lower the theoretical dose. In addition, it is higher with the emulsifier Plurol stéarique than with the emulsifier Labrafil.

Summarising, the films studied produce, in vivo within at least 8 hours, circulating plasma concentrations of isosorbide dinitrate which reach levels which have proved to be effective in human therapy, and the release of isosorbide dinitrate from the support is prolonged.

The following Examples show how the invention may be applied in practice.

EXAMPLE 1

A mixture of an ethanolic solution of isosorbide dinitrate (20 g/liter; 30 cm$^3$) with Plurol stéarique (0.6 g) is prepared. After evaporation of the solvent, a mixture of isosorbide dinitrate (0.6 g) and non-ionic emulsifier (0.6 g) is obtained.

A collodion is prepared by stirring a polyurethane POEG/POPG (POEG/POPG=75/25) copolymer (4.8 g) in dimethylformamide (48 cc) at a temperature of 60° C. for 5 hours.

The mixture of isosorbide dinitrate and non-ionic emulsifier (1.2 g) is added to the collodion (53 cc) prepared above. After partial evaporation of the dimethylformamide under reduced pressure, the collodion is poured onto a glass plate using a pourer which can be adjusted manually. The dimethylformamide is evaporated under reduced pressure (200 mm Hg; 26.6 kPa) at 60° C. for 12 hours hours.

A film which has an elastomeric appearance and is packed for use after cutting into unit doses is thus obtained.

The polyurethane/polyoxyethylene glycol/polyoxypropylene glycol polymer can be prepared in the following manner: The polyoxyethylene glycol functionalised at the $\alpha,\omega$-positions by reaction with a diisocyanate is prepared by reacting, at 80° C. for 1.5 hours, diphenylmethane diisocyanate (MDI) with $\alpha,\omega$-dihydroxy-polyoxyethylene glycol (molecular weight=1,500), which has first been dehydrated under reduced pressure (0.2 mm Hg; 0.026 kPa) at 60° C. in the presence of malonitrile as an inhibitor of secondary reactions.

The polyoxypropylene glycol functionalised at the $\alpha,\omega$-positions by reaction with a diisocyanate is prepared by reacting, at 80° C. for 40 minutes, diphenylmethane diisocyanate (MDI) with the $\alpha,\omega$-dihydroxypolyoxypropylene glycol (molecular weight=2,000), using "Stavinor" as the catalyst and malonitrile as an inhibitor of secondary reactions.

The two reaction mixtures are then diluted to 20% with dimethylformamide to stabilise the reaction of the isocyanate groupings with the hydroxyl groupings.

The two polymer solutions are mixed in suitable proportions and the polymers are coupled by means of propane-1,2-diamine so that the ratio of amine/isocyanate is equal to 0.95:1, this ratio being directly a function of the molecular weight of the polymer obtained (71,000 daltons).

The 20% collodion in dimethylformamide is poured into water containing 1% of sodium chloride. The polymer is recovered by centrifugation and washed twice with distilled water and then dried in an oven at 50° C. under reduced pressure (200 mm Hg; 26.6 kPa).

EXAMPLE 2

The polymer which is commercially available under the name Pellethane 2102-75 (4.8 g) is dissolved in dimethylformamide (46 g).

A mixture of an ethanolic solution of isosorbide dinitrate (20 g/liter; 30 cc) and Plurol stéarique (0.6 g) is prepared. The alcohol is evaporated under reduced pressure (100 mm Hg; 13.3 kPa) at 50° C.

The residual oil is added to the collodion of the polymer prepared above. After homogenisation, a slightly cloudy collodion is obtained, the composition of which is as follows:

| | |
|---|---|
| dimethylformamide | 88.5% |
| Pellethane 2102-75 polymer | 9.2% |
| isosorbide dinitrate | 1.15% |
| Plurol isostearique | 1.15% |

The collodion is poured onto a plate in the form of a film, the initial thickness of which is 0.6 mm. The dimethylformamide is evaporated under reduced pressure (100 mm Hg; 13.3 kPa) at 60° C. for 12 hours. A slightly cloudy film containing 10% of isosorbide dinitrate is obtained, from which discs 45 mm in diameter are cut.

The absorption of moisture in an atmosphere saturated with water is about 5%.

Release is effected in an aqueous medium and the isosorbide dinitrate released is analysed by high pressure liquid chromatography. The results are summarised in the following table:

| | Time (hours) | | | | |
|---|---|---|---|---|---|
| | 1 | 4 | 24 | 48 | 72 |
| % of isosorbide dinitrate released | 8.7 | 2.9 | 51 | 55.4 | 65.6 |

EXAMPLE 3

The procedure followed is the same as that in Example 2, but using methyl ethyl ketone as the solvent, a polymer marketed under the name Estane, and Transcutol as the emulsifier. A slightly cloudy collodion is obtained, the composition of which is as follows:

| | |
|---|---|
| methyl ethyl ketone | 67% |
| Estane polymer | 23.1% |
| isosorbide dinitrate | 3.3% |
| Transcutol | 6.6% |

The collodion is poured onto a plate in the form of a film, the initial thickness of which is 1.25 mm. The methyl ethyl ketone is evaporated under reduced pressure (100 mm Hg; 13.3 kPa) at 60° C. for 12 hours.

Discs 45 mm in diameter containing 10% of isosorbide dinitrate are cut out and are hydrated in a saturated atmosphere.

The results of the release in an aqueous medium are summarised in the following table:

| | Time (hours) | | | | |
|---|---|---|---|---|---|
| | 1 | 4 | 24 | 48 | 72 |
| % of isosorbide dinitrate released | 11.7 | 17.7 | 68 | 83.4 | 92.5 |

EXAMPLE 4

A solution consisting of methyl ethyl ketone (9 g), ketoprofen (3.2 g) and Labrasol (0.8 g) is added to a collodion (40 g) composed of methyl ethyl ketone (28 g), Estane (9.6 g) and Labrasol (2.4 g).

After homogenisation for 10 minutes at 45° C. under a nitrogen atmosphere, a clear collodion is obtained, the composition of which is as follows:

| | |
|---|---|
| methyl ethyl ketone | 69.8% |
| Estane | 18.1% |
| ketoprofen | 6.05% |
| Labrasol | 6.05% |

The collodion is poured onto a plate in the form of a film, the initial thickness of which is 1 mm. After evaporaton of the solvent under the usual conditions, a homogeneous transparent film containing 20% of ketoprofen is obtained, and is transferred onto silicone-coated paper.

Discs 45 mm in diameter are cut out. The absorption of moisture in an atmosphere saturated with water is about 69%.

The results of the release of ketoprofen in pure water are summarised in the following table: (the ketoprofen is analysed by analysis by ultraviolet spectroscopy at 255 nm).

| | | Time (hours) | | | | | | |
|---|---|---|---|---|---|---|---|---|
| | | 0.5 | 1 | 4 | 6 | 22 | 30 | 93 | 105 |
| % of ketoprofen separated out | 1st test | 1.9 | 3.6 | 7.5 | 11.2 | 23 | 24.6 | 30.5 | 32.6 |
| | 2nd test | 1.8 | 3.5 | 7.2 | 9.8 | 18.5 | 21.6 | 26 | 29.4 |
| | 3rd test | 2.3 | 3.5 | 9.1 | 11.6 | 18.8 | 21.4 | 29.6 | 38.7 |

EXAMPLE 5

A collodion is prepared, the composition of which is as follows:

| | |
|---|---|
| methyl ethyl ketone | 64.4% |
| ethanol | 14.4% |
| water | 3% |
| Estane | 11% |
| acebutolol hydrochloride | 3.6% |
| Labrasol | 3.6% |

(Since acebutolol hydrochloride is soluble in water, it is necessary to add ethanol and water to obtain a homogeneous transparent collodion).

The film is prepared and dried under the conditions described in Example 2. A translucent film strewn with crystals and containing 20% of acebutolol hydrochloride is obtained.

The results of the release of the acebutolol hydrochloride in an aqueous medium are summarised in the following table: (the acebutolol hydrochloride is analysed by analysis by ultraviolet spectroscopy at 235 mm)

| | | Time (hours) | | | |
|---|---|---|---|---|---|
| | | 0.25 | 0.50 | 1 | 2 |
| % of acebuto- | 1st test | 30.8 | 41.1 | 58.3 | 89.3 |
| lol hydrochlor- | 2nd test | 28.6 | 33.6 | 52.3 | 88.7 |
| ide release | 3rd test | 23.8 | 30.1 | 39 | 94.4 |

EXAMPLE 6

A collodion having the following composition is prepared:

| | |
|---|---|
| methyl ethyl ketone | 58% |
| 95° ethanol | 12% |
| Estane | 18% |
| nicergoline tartrate | 6% |
| Labrasol | 6% |

The collodion is poured onto a plate in the form of a film, the initial thickness of which is 0.5 mm. After drying under the usual conditions, an almost transparent homogenous film containing 20% of nicergoline tartrate is obtained. Discs 45 mm in diameter are cut out.

The results of the release of the nicergoline hydrochloride in an aqueous medium are summarised in the following table: (the nicergoline tartrate is analysed by ultraviolet spectroscopy at 277 nm).

| | | Time (hours) | | | |
|---|---|---|---|---|---|
| | | 0.25 | 0.75 | 1.25 | 3.25 |
| % of nicergoline | 1st test | 1.32 | 3.5 | 14.1 | 52.8 |
| tartrate released | 2nd test | 0.75 | 5.9 | 16.7 | 43.1 |

EXAMPLE 7

A homogeneous collodion having the following composition is prepared:

| | |
|---|---|
| methyl ethyl ketone | 37.7% |
| chloroform | 37.7% |
| polymer | 18.1% |
| metopimazine | 2% |
| Labrasol | 4.5% |

The collodion is poured onto a plate in the form of a film, the initial thickness of which is 1 mm. After drying under the usual conditions, a slightly yellow, homogeneous, translucent film containing 8.1% of metopimazine is obtained. Discs 45 mm in diameter are cut out.

The results of the release of the metopimazine in an aqueous medium are summarised in the following table: (the metopimazine is analysed by the ultraviolet spectroscopy at 263 nm)

| | | Time (hours) | | | | | | | |
|---|---|---|---|---|---|---|---|---|---|
| | | 0.5 | 1 | 4.5 | 6 | 21 | 45 | 142 | 190 |
| % of metopi- | 1st test | 0.36 | 1.3 | 4.7 | 5.1 | 12.1 | 27.3 | 60.2 | 75.3 |
| mazine released | 2nd test | 0.50 | 3 | 4.7 | 5 | 15.7 | 23.5 | 69.2 | 78.3 |

EXAMPLE 8

Isosorbide dinitrate (30 g) and non-ionic emulsifier (Labrasol) (30 g) are dissolved in methyl ethyl ketone (437 cc). Polyurethane granules (Estane 5702) (90 g) are introduced into the solution, with vigorous stirring. Stirring is maintained for 1 hour. The collodion thus obtained is left to stand for 14 hours in order to remove the bubbles. A constant thickness of collodion is spread on a double-faced strip of silicone-coated paper, which is passed through a ventilation tunnel and into an oven heated at 70°-80° C. for effective removal of the solvent by evaporation. The active film/silicone-coated paper complex is rolled up on itself to allow storage.

The active film thus prepared is then fixed, by transfer, onto a strip of protective support for the active film (polyethylene, PVC or Terphane, which may be alumina-treated and pigmented).

An adhesive film which has been prepared beforehand by coating onto anti-adhesive paper is deposited, by transfer, onto the active portion of film covered by a protective support. A complex consisting of a layer of protective support, the active film, the adhesive film and the anti-adhesive paper, is thus obtained. The adhesive film consists of a material which is sensitive to pressure, such as copolymers of polyacrylates or polymethacrylates, polyvinyl alkyl ethers, polyurethanes, polyesters, polyamides, copolymers of ethylene/vinyl acetate, styrene/isoprene block copolymers, polyisobutylene rubbers or silicone resins.

The complex thus prepared is then cut with a punch to the desired shape and size. The "patches" thus obtained are placed in heat-sealed sachets suitably chosen for prolonged storage.

It may be advantageous to cut the active film before transferring it to the protective support and to cut a complex (adhesive film) of greater surface area than that of the active film in order to obtain an adhesive composition around the periphery of the active film.

The adhesive film may be charged with active ingredient (1 to 10%) in order to avoid a delay time in the release of the active ingredient.

We claim:

1. A transdermal medicament comprising 10 to 20% of a transdermally active ingredient selected from the group consisting of antianginal agents, antiemetic agents, anticholinergic agents, non-steroid anti-inflammatory agents, steroid anti-inflammatory agents, antihypertensive agents, beta-blockers, vasodilators, neuroleptic agents, tranquillizers, bronchodilators, antispasmodic agents and hormones and 10 to 20% of a nonionic emulsifying agent selected from the group consisting of polycondensates of ethylene oxide with a fatty acid or fatty alcohol, sorbitan esters, triglycerides with free hydroxyl group, polypropylene glycol monoglycerides and polyglycerol esters, the said active ingredient being dispersed in crystalline or solubilized form in a non-crosslinked, film-forming homogeneous, thermoplastic, elastomeric, water-insoluble polymer selected from the group consisting of polyurethanes based on a polyether or polyester, polyamides, polyesters, polyethers, and polyolefins, the said percentages being by weight based on the said film-forming polymer.

2. A transdermal medicament comprising 5 to 20% of a transdermally active ingredient selected from the group consisting of antianginal agents, antiemetic agents, anticholinergic agents, non-steroid anti-inflammatory agents, steroid anti-inflammatory agents, antihypertensive agents, beta-blockers, vasodilators, neuroleptic agents, tranquillizers, bronchodilators, antispasmodic agents and hormones, 5 to 30% of a non-ionic emulsifying agent selected from the group consisting of polycondensates of ethylene oxide with a fatty acid or fatty alcohol, sorbitan esters, triglycerides with free hydroxyl groups, polypropylene glycol monoglycerides and polyglycerol esters, and 1 to 30% of a copolymer containing a hydrophobic sequence which migrates to the surface of the said medicament to form a homogeneous membrane which provides complementary control of the release of the transdermally active ingredient, the said active ingredient being dispersed in crystalline or solubilized form in a non-crosslinked, film-forming homogeneous, thermoplastic, elastomeric, water-insoluble polymer selected from the group consisting of polyurthanes based on a polyether or polyester, polyamides, polyesters, polyethers, and polyolefines, the said percentages being by weight based on the said film-forming polymer.

3. A medicament according to claim 1 in which the homogeneous thermoplastic polymer is a polyurethane/polyoxyethylene glcyol/polyoxypropylene glycol copolymer or a polyurethane based on polytetramethylene glycol, polycaprolactone or polyadipate.

4. A medicament according to claim 1, in which the non-ionic emulsifier is polyglycerol palmitostearate, polyglycerol isostearate, sucrose monopalmitate, polyoxymethylene oleyl glyceride, diethylene glycol monoethyl ether, or a polyoxymethyleneated $C_8$–$C_{10}$-glyceride.

5. A medicament according to clalim 2, in which the said hydrophobic copolymer is a polydimethylsiloxane polyoxyethylene glycol copolymer.

6. A medicament according to claim 1, which is covered by an adhesive.

7. A medicament according to claim 1, in which the transdermally active ingredient is isosorbide dinitrate, isosorbide monoitrate, trinitrin, metopimazine, dimenhydrinate, scopolamine, ketoprofen, prednisolone, dexamethazone, clonidine, acebutolol, nicergoline, a neuroleptic phenothiazine, a tranquilling benzodiazepine, suriclone, suproclone, phenylpropanolamine, butylhyoscine bromide, or estradiol.

8. A transdermal medicament according to claim 1 packaged in a unit dose.

9. Method of administering a medicament to a patient which comprises applying to the skin of the said patient a transdermal medicament as claimed in claim 1 whereby an effective amount of the transdermally active ingredient in the said medicament is absorbed by the said patient.

10. A medicament according to claim 1 in which the active ingredient is isosorbide dinitrate, the non-ionic emulsifier is polyglycerol palmitostearate, and the thermoplastic elastomeric polymer is a polyurethane/polyoxyethylene glycol/polyoxypropylene glycol copolymer.

11. A medicament according to claim 2 in which the homogeneous thermoplastic polymer is a polyurethane/polyoxyethylene glycol/polyoxypropylene glycol copolymer, or a polyurethane based on polytetramethylene glycol, polycaprolactone or polyadipate.

12. A medicament according to claim 2, in which the non-ionic emulsifier is polyglycerol palmitostearate, plyglycerol isostearate, sucrose monopalmitate, polyoxymethylene oleyl glyceride, diethylene glycol monoethyl ether or a $C_8$–$C_{10}$-glyceride.

13. A medicament according to claim 2, which is covered by an adhesive.

14. A medicament according to claim 2, in which the transdermally active ingredient is isosorbide dinitrate, isosorbide monoitrate, trinitrin, metopimazine, dimenhydrinate, scopolamine, ketoprofen, predinsolone, dexamethazone, clonidine acebutolol, nicergoline, a neuroleptic phenothiazine, a tranquillising benzodiazepine, suriclone, suproclone, phenylpropanolamine, butylhyoscine bromide, or estradiol.

15. A transdermal medicament according to claim 2 packaged in a unit does.

16. A medicament according to claim 2 in which the active ingredient is isosorbide dinitrate, the non-ionic emulsifier is polyglycerol palmitostearate, and the thermoplastic elastomeric polymer is a polyurethane/polyoxyethylene glycol/polyoxypropylene glycol copolymer.

17. Method of administering a medicament to a patient which comprises applying to the skin of the said patient a transdermal medicament as claimed in claim 2 whereby an effective amount of the transdermally active ingredient in the said medicament is absorbed by the said patient.

18. A transdermal medicament according to claim 2 in which the transdermally active ingredient is isosorbide dinitrate, the non-ionic emulsifier is polyglycerol palmitostearate, the hydrophobic copolymer is polydimethylsiloxane/polyoxyethylene glycol copolymer, and the thermoplastic elastomeric polymer is a polyurethane/polyoxyethylene glycol/polyoxypropylene glycol copolymer.

* * * * *